United States Patent [19]
Harrison et al.

[11] Patent Number: 5,999,842
[45] Date of Patent: Dec. 7, 1999

[54] FUNCTIONAL THERMAL IMAGING APPARATUS

[75] Inventors: Richard Alan Harrison, Irvine, Calif.; Mark David Parsons, North Ogden, Utah

[73] Assignee: Computerized Thermanl Imaging Company, Bingham Farms, Mich.

[21] Appl. No.: 08/864,752

[22] Filed: May 29, 1997

[51] Int. Cl.⁶ ..................................................... A61B 5/00
[52] U.S. Cl. ........................................... 600/474; 600/549
[58] Field of Search .................................... 600/473, 474, 600/549, 407; 378/37; 250/339.04, 339.03

[56] References Cited

U.S. PATENT DOCUMENTS

| | | |
|---|---|---|
| 3,533,223 | 10/1970 | Olsson . |
| 3,591,713 | 7/1971 | Olsson et al. . |
| 3,604,932 | 9/1971 | Beach . |
| 3,830,970 | 8/1974 | Hurley et al. . |
| 4,043,757 | 8/1977 | Wagstaff . |
| 4,135,497 | 1/1979 | Meyers et al. . |
| 4,233,988 | 11/1980 | Dick et al. . |
| 4,366,381 | 12/1982 | Fischer et al. . |
| 4,416,552 | 11/1983 | Hessemer, Jr. et al. . |
| 4,428,382 | 1/1984 | Walsall et al. . |
| 4,608,991 | 9/1986 | Rollwitz . |
| 4,627,442 | 12/1986 | Land . |
| 4,691,712 | 9/1987 | Brown, Jr. . |
| 4,849,885 | 7/1989 | Stillwagon et al. . |
| 4,854,724 | 8/1989 | Adams et al. . |
| 4,920,973 | 5/1990 | Tanaka et al. . |
| 4,995,398 | 2/1991 | Turnidge . |
| 5,056,525 | 10/1991 | Hafezi . |
| 5,115,815 | 5/1992 | Hansen . |
| 5,692,511 | 12/1997 | Grable . |
| 5,779,635 | 7/1998 | Carr . |
| 5,803,082 | 9/1998 | Stapleton et al. . |

OTHER PUBLICATIONS

Nyirjesy, I. Breast Thermography. *Clinical Obstetrics and Gynecology*, 25 (2): 401–408, 1982.

*Primary Examiner*—Marvin M. Lateef
*Assistant Examiner*—Shawna J. Shaw
*Attorney, Agent, or Firm*—Tarolli, Sundheim, Covell, Tummino & Szabo LLP

[57] ABSTRACT

A thermal imaging apparatus (10) includes a table (12) having an opening 48 through which a prone patient's breast (24) can be suspended freely downward. The apparatus (10) further includes an air handling apparatus (14) which chills ambient air and directs the chilled air against the suspended breast (24), a thermal radiation sensor (16), and a mirror assembly (18, 20) which reflects thermal radiation from the suspended breast (24) to the sensor (16).

19 Claims, 4 Drawing Sheets

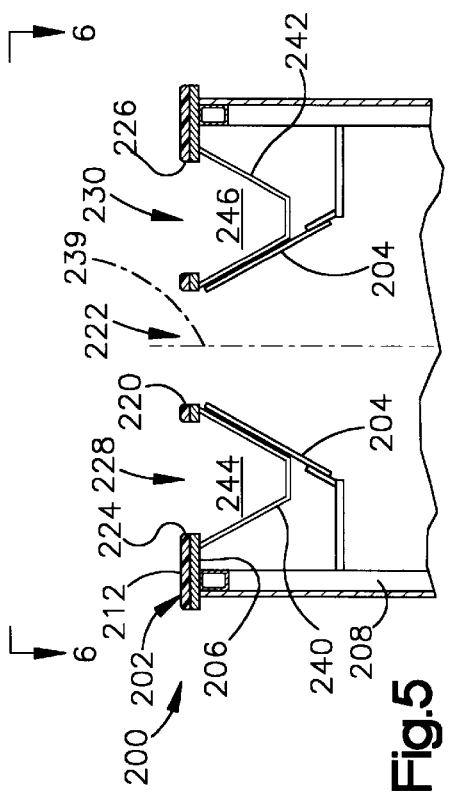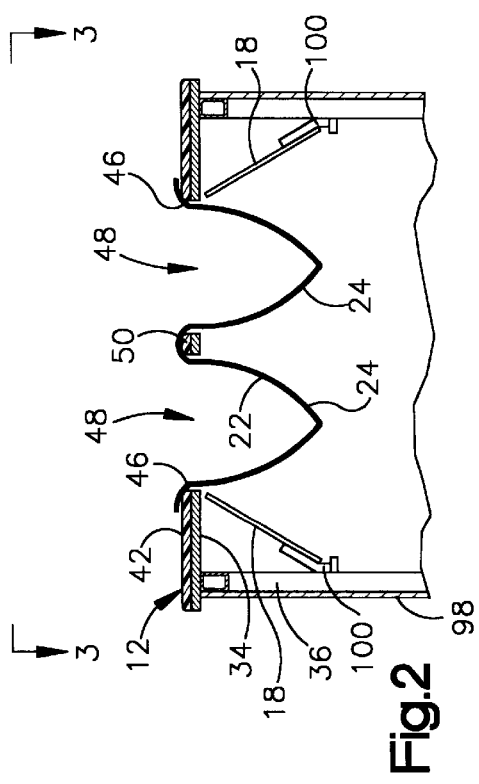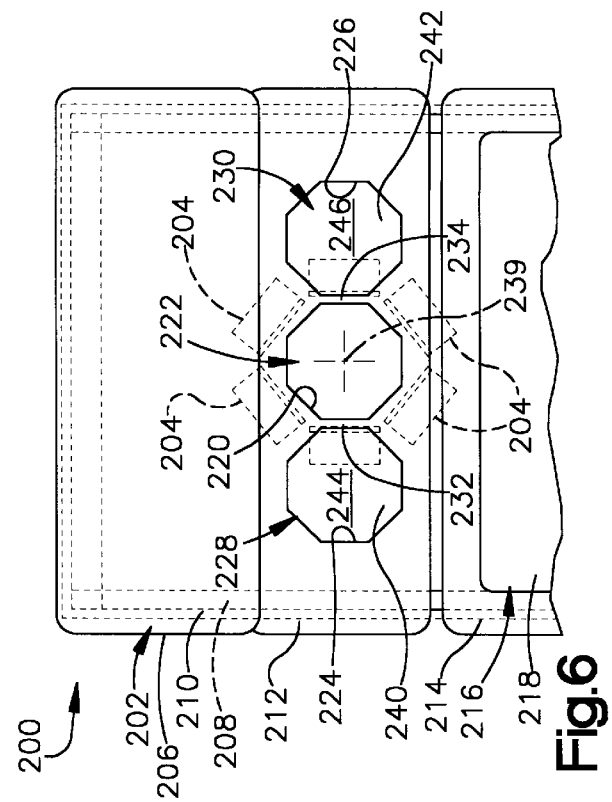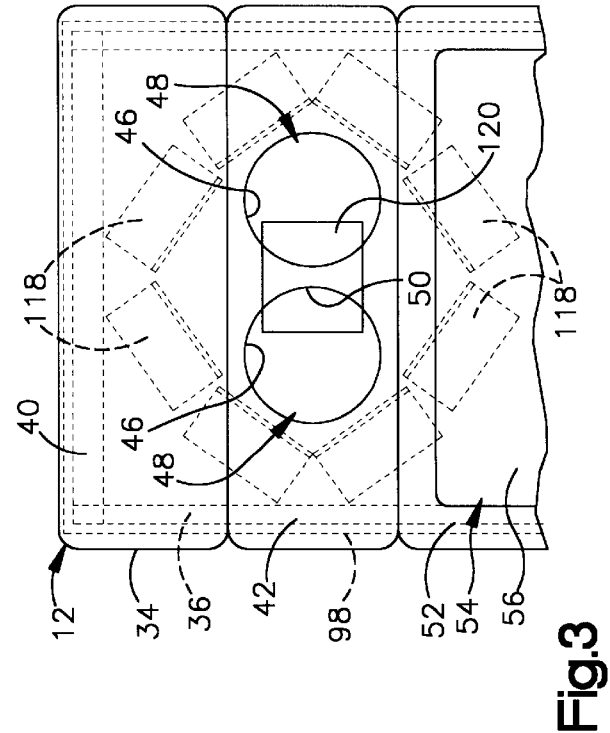

FUNCTIONAL THERMAL IMAGING APPARATUS

FIELD OF THE INVENTION

The present invention relates to medical thermal imaging, and particularly relates to an apparatus for thermal imaging of a patient's breasts.

BACKGROUND OF THE INVENTION

Cancers in breasts are masses of cells which may have an increased blood supply, perhaps with an underdeveloped or non-existent nervous system and/or an increased metabolic rate. Any of these mechanisms can contribute to a greater capacity, as compared to that of normal tissue, to deliver heat to the overlying skin when cooled.

Breast thermal imaging is a method of examining a patient's breasts by cooling the skin while imaging the skin surface temperature. A region of skin with warmer surface temperatures or reduced cooling rates relative to the surrounding areas may indicate a relatively greater capacity for heating and hence a possible cancerous mass.

Current thermal imaging equipment requires a patient to stand or sit upright while room temperature air is blown by fans to cool the breasts while they are being imaged. This may lead to three difficulties. First, breathing movement by the patient causes image registration problems. Second, gravity acting on the breasts while the patient's torso is in a vertically upright position may cause occlusion along the bottom of the breasts. Third, the angle of the image rays relative to the top, bottom and sides of the breasts may approach a tangent, causing poor image resolution at those areas.

SUMMARY OF THE INVENTION

In accordance with a principal feature of the present invention, a thermal imaging apparatus comprises a table having an opening through which a prone patient's breast can be suspended freely downward. The apparatus further comprises a thermal radiation sensor and a mirror assembly which reflects thermal radiation from the suspended breast to the sensor.

In the preferred embodiments of the present invention, the mirror assembly includes a plurality of upper mirrors in a circular array extending circumferentially around the suspended breast. The upper mirrors face horizontally inward toward top, bottom and side portions of the suspended breast. The upper mirrors further have inclined orientations extending vertically downwards and horizontally outward from the suspended breast. In this arrangement, the total reflective surface area defined by the upper mirrors has a conical configuration extending circumferentially around the suspended breast so as to reflect thermal radiation from all or substantially all of the top, bottom and side portions of the suspended breast.

The preferred embodiments of the present invention further include a lower mirror which faces vertically upward. The lower mirror reflects thermal radiation from the suspended breast, and also from the upper mirrors, to the sensor. The lower mirror can be omitted if a sensor with a sufficiently wide field of view is located directly beneath the upper mirrors.

In accordance with another principal feature of the present invention, the apparatus comprises an air handling system which chills ambient air and directs the chilled air to flow against the patient's suspended breast. Further in accordance with this feature of the present invention, the table has an inner opening located between two outer openings. The prone patient can move across the table between a left side position and a right side position. In each position, a corresponding one of the patient's breasts is suspended freely downward through the inner opening. A shield assembly blocks the chilled air from affecting the temperature of the other breast beneath either of the outer openings. Since the shielded breast is protected from the chilled air while the unshielded breast is being examined by cooling and thermal imaging, it does not have to be rewarmed before it can be examined under the same conditions. The present invention thus enables the breasts to be examined by cooling and thermal imaging individually without a delay between the first and second examinations.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 2 is a view taken on line 2—2 of FIG. 1;

FIG. 3 is a view taken on line 3—3 of FIG. 2;

FIG. 5 is a schematic view of parts of a thermal imaging apparatus comprising a second embodiment of the present invention;

FIG. 6 is a view taken on line 6—6 of FIG. 5; and

DESCRIPTION OF PREFERRED EMBODIMENTS

Figure 1:
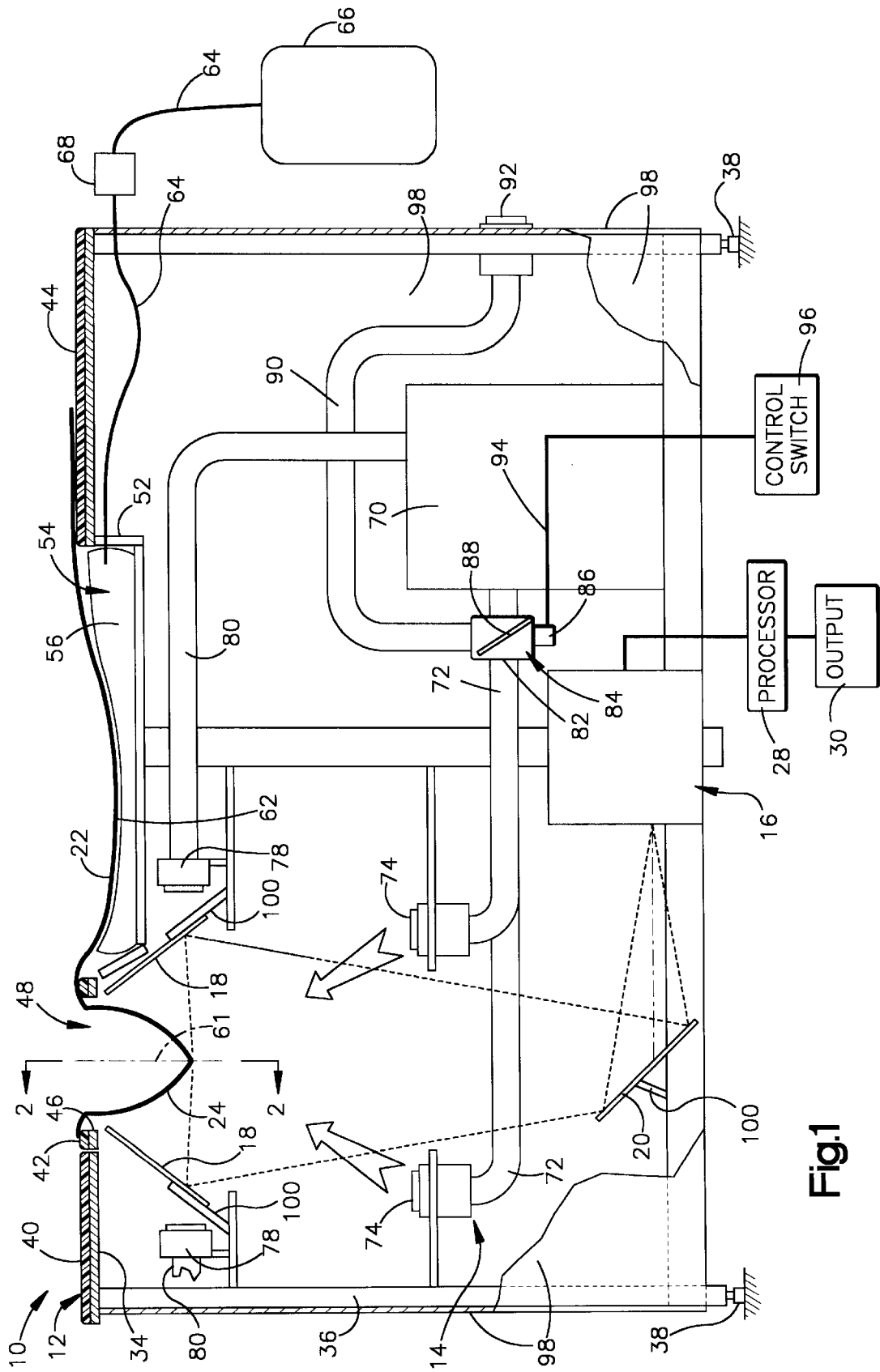
FIG. 1 is a schematic view of a thermal imaging apparatus comprising a first embodiment of the present invention.

A thermal imaging apparatus 10 comprising a first embodiment of the present invention is shown schematically in FIG. 1. The apparatus 10 includes a table 12 for supporting a patient in a prone position. The apparatus 10 further includes an air handling system 14, a thermal radiation sensor 16, and an assembly of mirrors. The mirrors include upper mirrors 18 and a lower mirror 20.

When a patient lies prone upon the table 12, the frontal surfaces of the patient's torso follow the contour indicated by the bold line 22 shown in FIGS. 1 and 2. The patient's breasts 24 are then exposed to chilled air provided by the air handling system 14. As the surfaces of the breasts 24 are cooled by the chilled air, the upper mirrors 18 reflect thermal radiation from the breasts 24 to the lower mirror 20. The lower mirror 20 reflects thermal radiation from the breasts 24 and the upper mirrors 18 to the sensor 16. A microprocessor 28 interprets and responds to the output of the sensor 16 by directing an output device 30 to produce one or more thermal images of the breasts 24. The thermal images of the breasts 24 may have any suitable format known in the art such as, for example, images on the screen of a cathode ray tube.

The table 12 in the first embodiment of the present invention is a free standing structure including a table top 34 and a support frame 36 with leveling adjustors 38. The table top 34 includes a padded head panel 40, a padded chest panel 42, and a padded leg panel 44. The chest panel 42 has a pair of inner edge surfaces 46 defining a pair of breast openings 48. As shown in FIGS. 2 and 3, the breast openings 48 are separated by a sternum support portion 50 of the chest panel 42. An intermediate panel structure 52 defines a recess 54 between the chest panel 42 and the leg panel 44. An optional inflatable cushion 56 is received in the recess 54.

The table top 34 and the cushion 56 together support the patient in the prone position indicated by the bold line 22. Importantly, the patient's breasts 24 extend vertically through the breast openings 48 and are spaced horizontally from the surrounding inner edge surfaces 46 of the chest panel 42. The breasts 24 are thus suspended freely downward through the openings 48. By suspended freely downward it is meant that the breasts 24 hang downward without support from adjacent portions of the patient's chest, the chest panel 42, or other parts of the apparatus 10, and have longitudinal centerlines 61 which are vertical or substantially vertical. This ensures that all of the top, bottom and side surface portions of the breasts 24 are exposed without occlusion circumferentially entirely around the centerlines 61.

The cushion 56 directly supports the patient's stomach 62 for comfort. The cushion 56 also helps to support the patient's torso such that movement caused by breathing occurs primarily at the rear of the chest. This helps to minimize movement of the breasts 24, and thereby to maintain good registration between successive thermal images of the breasts 24. An inflator system including pneumatic conduits 64, a source 66 of compressed air, and an inlet/outlet control valve 68, each of which may have any suitable structure known in the art, is used to control inflation of the cushion 56 as needed for each individual patient.

The air handling system 14 includes a source 70 of chilled air. A plurality of delivery ducts 72 have vents 74 which direct chilled air from the source 70 to flow beneath the table top 34 toward and against the top, bottom and side surfaces of the prone patient's suspended breasts 24. Factors that influence the body's heating of the skin of the breasts 24 such as, for example, breast carcinomas, can then become evident as temperature gradients develop across the chilled surface areas.

In the first embodiment of the present invention, the source 70 of chilled air is a conventional room air conditioner which chills ambient air to a temperature within a range extending from about 50° F. to about 55° F. The apparatus 10 can be used to examine the breasts 24 by thermal imaging before, during, and/or upon completion of exposure to the chilled air, or upon rewarming of the breasts 24.

The air handling system 14 in the first embodiment further includes a plurality of additional vents 78 and return ducts 80 for conveying chilled air back to the source 70 for recycling. A diverter 82 is comprised of a chamber 84, an actuator 86, at least one damper plate 88. The actuator 86 will move the damper plate(s) 88 such that the chilled air from the source 70 is diverted through an exhaust duct 90 to an exhaust vent 92 and not allowed to pass through the delivery ducts 72, or instead allowed to pass through the delivery ducts 72 and not the exhaust duct 90. The actuator is controlled via a control wire 94 and a control switch 96. The operator of the apparatus 10 (or a computer) will use the switch 96 to control the diverter 82 to direct chilled air from the source 70 either toward the breast openings 48 via the delivery ducts 72 and vents 74, or away from the breast openings 48 to the outside of the table 12 via the exhaust duct 90 and exhaust vent 92. This ability to divert the air flow prevents cooling of the breasts 24 while the operator is helping the patient into or out of position on the table 12. This in turn allows thermal imaging of the breasts 24 in an equilibrium state at a constant room temperature, and then by fast application of the chilled air to thermally image the skin surface temperature response to a sudden drop in temperature. The entire air handling system 14 is preferably mounted on the frame 36 so as to be movable with the table 12 as part of a unitary apparatus 10. A peripheral side panel structure 98 also is mounted on the frame 36. The side panel structure 98 encloses the air handling system 14 and the mirrors 18 and 20 around the periphery of the table 12.

As shown in FIG. 2, the upper mirrors 18 are arranged beneath the table top 34 in a generally circular array extending circumferentially around the suspended breasts 24. Each upper mirror 18 faces horizontally inward toward a corresponding top, bottom or side surface portion of one or both of the breasts 24. Each upper mirror 18 further has an inclined orientation extending vertically downward and horizontally outward from the breasts 24. The total reflective surface area of the upper mirrors 18 thus has an effectively conical configuration extending circumferentially around the breasts 24. This arrangement enables the upper mirrors 18 to reflect thermal radiation from all or substantially all of the top, bottom and side surface portions of the breasts 24 to the lower mirror 20.

As noted above, the lower mirror 20 reflects thermal radiation from the upper mirrors 18 to the sensor 16, and also reflects thermal radiation directly from the suspended breasts 24 to the sensor 16. The mirrors 18 and 20 in the first embodiment of the present invention have metallic (preferably gold) reflective surfaces. A plurality of brackets 100, which may be adjustable for individual patients, support the mirrors 18 and 20 on the frame 36.

The sensor 16 may comprise any known apparatus for sensing thermal radiation reflected by the mirrors 18 and 20. The sensor 16 in the first embodiment is an infrared image scanning device. As known in the art, such a device senses infrared radiation throughout a scanned field. The output of the device 16 is an electrical signal indicating the distribution and level of thermal radiation, and hence the distribution and level of surface temperatures, throughout the scanned field. An example of known infrared scanning devices that can be used in accordance with the present invention is the TIP-4 thermal image processor unit available from Bales Scientific Inc., of Walnut Creek, Calif. The microprocessor 28 and the output device 30 may comprise any suitable apparatus known in the art.

In accordance with a particular feature of the present invention, the inclined orientation of the upper mirrors 18 helps to optimize the thermal image resolution at the sensor 16. This feature of the present invention is illustrated more specifically in FIG. 4 with reference to the lower mirror 20, one of the breasts 24, and one of the upper mirrors 18.

Figure 4:
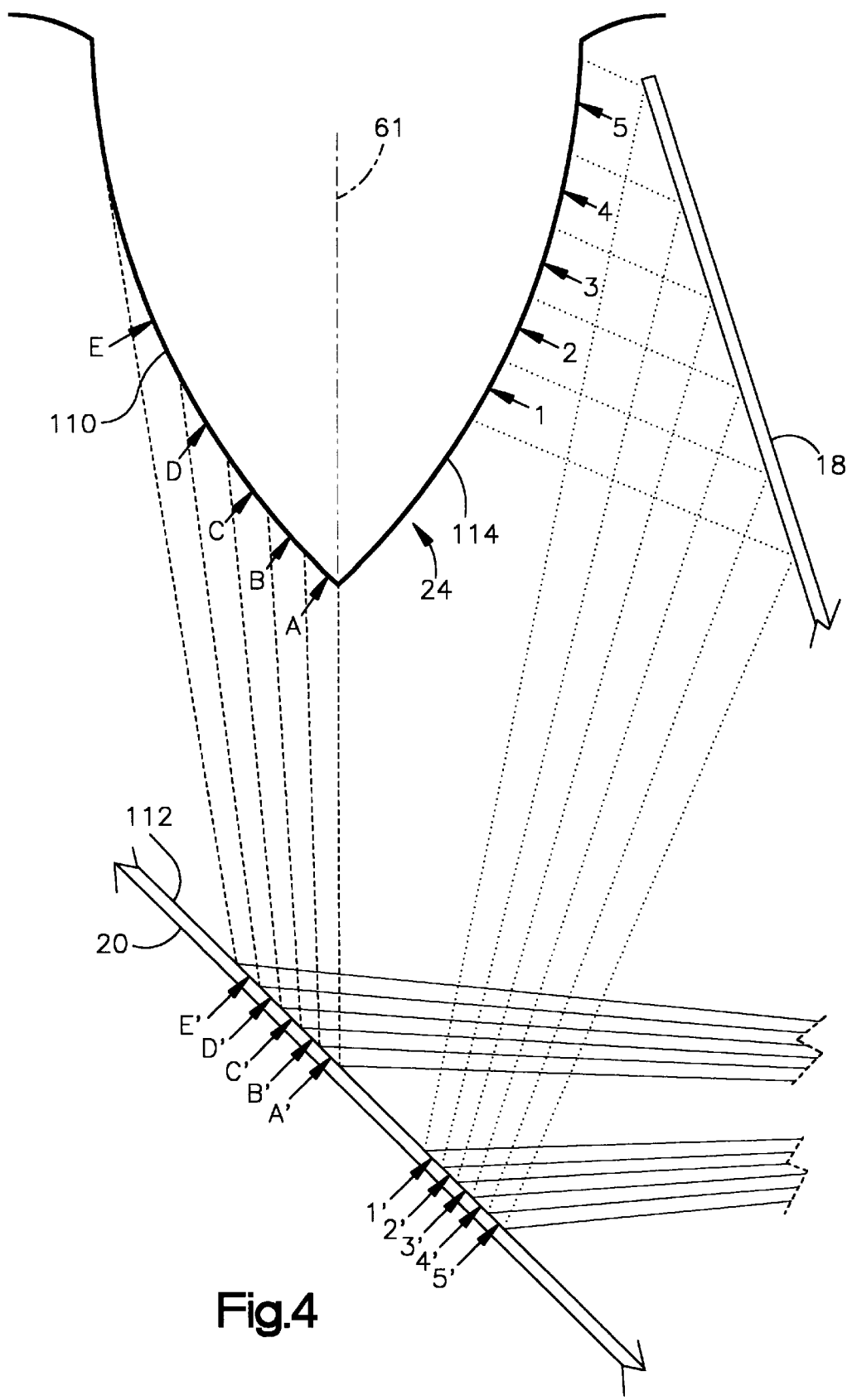
FIG. 4 is an enlarged partial view of parts of the apparatus of FIG. 1.

As shown in FIG. 4, some of the infrared radiation emitted from the curved top surface 110 of the breast 24 is transmitted directly to the reflective surface 112 of the lower mirror 20 in directions indicated by dashed lines. When compared with each other successively outward from the longitudinal centerline 61 of the breast 24, the dashed lines are seen to be increasingly inclined toward a tangent to the breast surface 110. The distance between each adjacent pair of those lines is greater at the breast surface 110 than at the reflective surface 112, which is planar. That difference increases progressively outward from the centerline 61. The areas identified by the letters A–E on the breast surface 110 likewise differ in size from the corresponding areas identified by the letters A'–E' on the reflective surface 112. This causes the thermal images reflected by the surface areas A'–E' to be contracted in amounts that increase progressively outward from the surface area A' to the surface area E'. Accordingly, the reflective surface areas A'–E', which are scanned by the sensor 16, are not equally representative of their corresponding breast surface areas A–E.

As further shown schematically in FIG. 4, some of the infrared radiation emitted from the curved bottom surface 114 of the breast 24 is reflected from the upper mirror 18 to the lower mirror 20 in directions indicated by dotted lines. Infrared radiation emitted from the curved surface areas 1–5 on the breast 24 is thus reflected to a plurality of corresponding planar surface areas 1'–5' on the lower mirror 20. As a result of the inclined orientation of the upper mirror 18, the dotted lines are nearly perpendicular, rather than tangential, to the breast surface 114. The distances between adjacent pairs of those lines is relatively consistent along the breast surface 114. It follows that the size differences between the reflective surface areas 1'–5' and the corresponding breast surface areas 1–5 are significantly less than the size differences between the reflective surface areas A'–E' and the corresponding breast surface areas A–E. Accordingly, the reflective surface areas 1'–5', which also are scanned by the sensor 16, are more closely representative of their corresponding breast surface areas 1–5. This improves the thermal image resolution at the sensor 16.

For the first embodiment, as shown in FIG. 3, the upper mirrors 18 are arranged beneath the table top 34 in a configuration such that they approximate a partial conical surface around the sides of the breasts 24 farthest from the centerline of the table 12, but extent longitudinally to meet at or near the centerline of the table 12 in front of and behind the breast openings 48. This configuration allows the thermal radiation from the skin on the side of the breasts 24 closest to the centerline to cross to the upper mirrors 18 on the opposite side of the centerline, and then reflect to the lower mirror 20 and/or the sensor 16. The top, bottom, and side surfaces farthest from the centerline of each breast are also reflected by this configuration to the lower mirror 20 and/or the sensor 16, thus providing full circumferential coverage of the skin of both breasts 24 in one image. Without this optical cross over, the side of each breast 24 closest to the centerline could be occluded by the opposite breast 24 when viewed by the sensor 16.

In a second embodiment of the present invention, a thermal imaging apparatus 200 includes an alternative table 202 and an alternative assembly of upper mirrors 204, as shown partially in the schematic views of FIGS. 5–8. Other parts (not shown) of the apparatus 200 include an air handling system, a thermal radiation sensor, and a lower mirror, each of which is substantially the same as the corresponding part of the apparatus 10 described above.

Like the table 12 in the first embodiment of the present invention, the table 202 in the second embodiment comprises a table top 206 supported on an enclosed frame 208. The table top 206 includes a padded head panel 210, a padded chest panel 212, and an unpadded intermediate panel 214 defining a recess 216 containing an optional inflatable cushion 218.

The table 202 has three separate breast openings in a row extending laterally across the table top 206. Specifically, an inner edge surface 220 of the chest panel 212 defines an inner breast opening 222 at the center of the table top 206. A pair of additional inner edge surfaces 224 and 226 define a respective pair of laterally outer breast openings 228 and 230 on opposite sides of the inner opening 222. A corresponding pair of sternum support portions 232 and 234 of the chest panel 212 separate the outer openings 228 and 230 from the inner opening 222.

The upper mirrors 204 together have a total reflective surface area with an effectively conical configuration extending circumferentially around the central axis 239 of the inner breast opening 222. More specifically, each upper mirror 204 faces horizontally inward toward the axis 239, and has an inclined orientation extending vertically downward and horizontally outward from the axis 239. Each upper mirror 204 is thus arranged to face horizontally inward toward a corresponding top, bottom or side surface portion of a patient's breast suspended freely downward through the inner opening 222, and also to reflect thermal radiation from the breast to the lower mirror in the manner described above with reference to FIG. 4.

The apparatus 200 further includes a breast shield assembly comprising first and second breast enclosure structures 240 and 242. The first breast enclosure structure 240 is supported by the chest panel 212 beneath the first outer breast opening 228. The second breast enclosure structure 242 is supported by the chest panel 212 beneath the second outer breast opening 230. The enclosure structures 240 and 242 define chambers 244 and 246 beneath the outer breast openings 228 and 230, respectively. When the air handling apparatus in the second embodiment of the present invention directs chilled air to flow beneath the chest panel 212, the breast enclosure structures 240 and 242 block the chilled air from entering the chambers 244 and 246.

Figure 7:
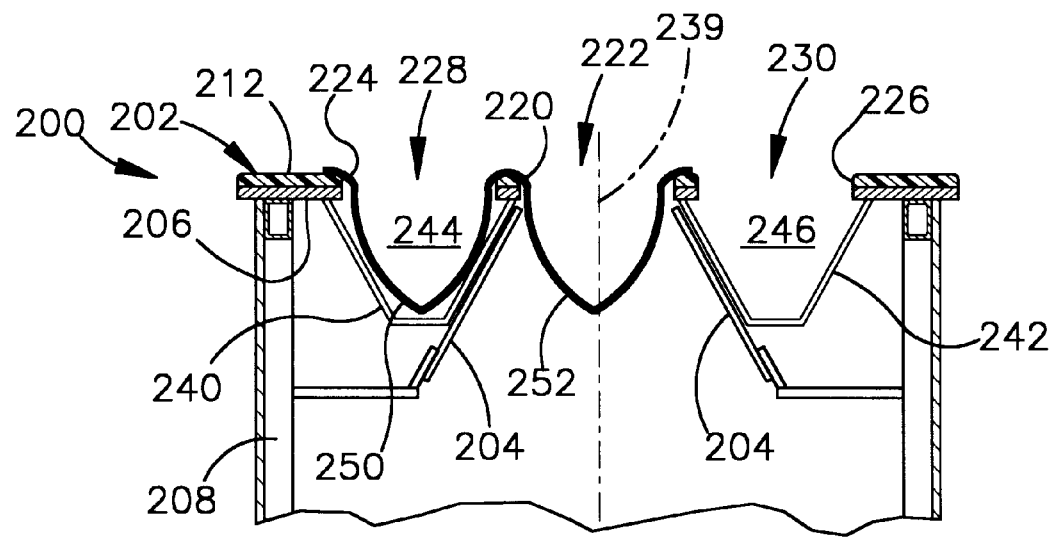
FIGS. 7 and 8 are views similar to FIG. 5 illustrating positions taken by a patient in use of the apparatus of FIG. 5.
Figure 8:
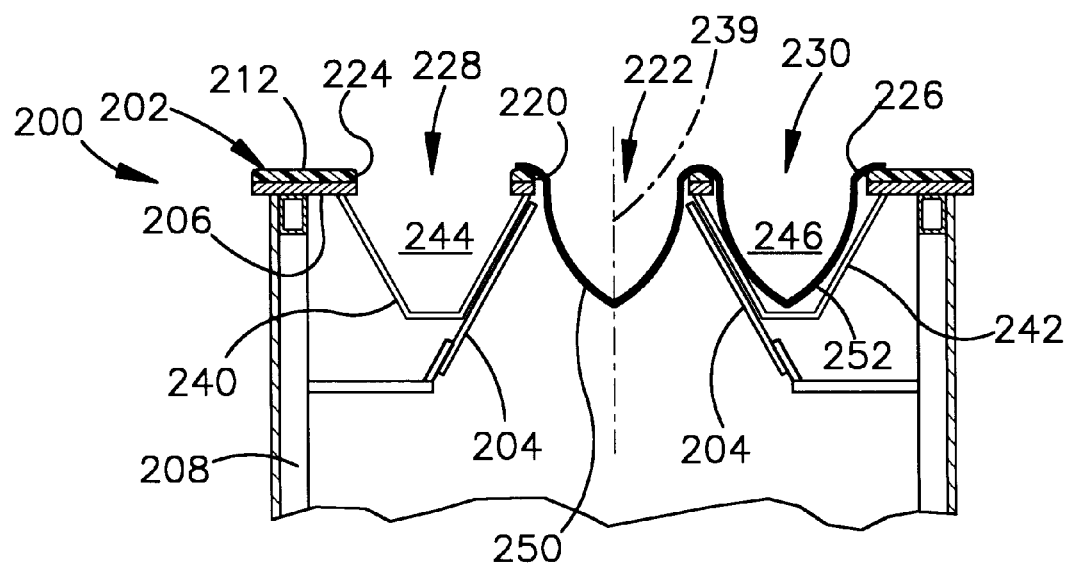

A patient can lie prone upon the table 202 in a left side position, as shown in FIG. 7, and alternately in a right side position, as shown in FIG. 8. When the patient is in the left side position, the left breast 250 is suspended freely downward into the first chamber 244 through the first outer opening 228. The right breast 252 is suspended freely downward through the inner opening 222. The first breast enclosure structure 240 then shields the left breast 250 from the chilled air beneath the table top 206 while the right breast 252 is exposed to the chilled air. This ensures that the chilled air does not affect the surface temperature of the left breast 250 while the right breast 252 is being cooled and thermally imaged beneath the table top 206. When the examination of the right breast 252 is completed, the patient can move to the right side position for subsequent cooling and thermal imaging of the left breast 250.

The present invention has been described with reference to preferred embodiments. Those skilled in the art may perceive improvements, changes and modifications. For example, the upper mirrors in the preferred embodiments have planar reflective surfaces. Each of those surfaces defines a segmental portion of a total reflective surface area having an effectively conical configuration extending circumferentially around the suspended breast(s). Curved reflective surfaces, or a greater number of planar reflective surfaces, could be used to define total reflective surface areas with more fully conical configurations. Such improvements, changes and modifications within the skill of the art are intended to be covered by the appended claims.

Having described the invention, the following is claimed:

1. Apparatus comprising:

a table having an opening through which a prone patient's breast can be suspended freely downward;

a thermal radiation sensor;

a mirror assembly configured to reflect thermal radiation from the suspended breast to said sensor, said mirror assembly defining a reflective surface area having an effectively conical configuration oriented to extend circumferentially around the suspended breast; and an air handling system including an air conditioning unit operative to chill ambient air, said air handling system being operative to direct said chilled air against the suspended breast.

2. Apparatus as defined in claim 1 wherein said mirror assembly further defines a lower reflective surface area oriented to face vertically upward toward the suspended breast and also toward said effectively conical reflective surface area so as to reflect thermal radiation from the suspended breast and also from said effectively conical reflective surface area.

3. Apparatus as defined in claim 1 further comprising an output device operative to produce a thermal image, and a microprocessor responsive to output of said sensor so as to direct said output device to produce a thermal image representative of thermal radiation reflected from the suspended breast to said sensor by said mirror assembly.

4. Apparatus as defined in claim 1 wherein said table has first, second and third openings in a row extending across said table, said first and second openings respectively providing clearance for a patients' left and right breasts to be suspended freely downward when the patient is in a first prone position on said table, said second and third openings respectively providing clearance for the patient's left and right breasts to be suspended freely downward when the patient is in a second, laterally shifted prone position on said table.

5. Apparatus comprising:
a table having an opening through which a prone patient's breast can be suspended freely downward;
a thermal radiation sensor;
a mirror assembly configured to reflect thermal radiation from the suspended breast to said sensor, said mirror assembly including a mirror oriented to face horizontally inward toward a top, bottom or side portion of the suspended breast, and to be inclined vertically downward and horizontally outward from the suspended breast; and
an air handling system including an air conditioning unit operative to chill ambient air, said air handling system being operative to direct said chilled air against the suspended breast.

6. Apparatus as defined in claim 5 wherein said mirror assembly further includes a lower mirror oriented to face vertically upward toward the suspended breast and also toward said horizontally facing mirror so as to reflect thermal radiation from the suspended breast and also from said horizontally facing mirror.

7. Apparatus as defined in claim 5 further comprising an output device operative to produce a thermal image, and a microprocessor responsive to output of said sensor so as to direct said output device to produce a thermal image representative of thermal radiation reflected from the suspended breast to said sensor by said mirror assembly.

8. Apparatus as defined in claim 5 wherein said table has first, second and third openings in a row extending across said table, said first and second opening, respectively providing clearance for a patients' left and right breasts to be suspended freely downward when the patient is in a first prone position on said table, said second and third openings respectively providing clearance for the patient's left and right breasts to be suspended freely downward when the patient is in a second, laterally shifted prone position on said table.

9. Apparatus comprising:
a table having first, second and third openings in a row extending across said table, said first and second openings respectively providing clearance for a patients' left and right breasts to be suspended freely downward when the patient is in a first prone position on said table, said second and third openings respectively providing clearance for the patient's left and right breasts to be suspended freely downward when the patient is in a second, laterally shifted prone position on said table;
an air handling system operative to chill ambient air and to direct said chilled air beneath said openings in said table;
a sensor operative to sense temperatures induced by said chilled air on the surface of one of the patient's breasts when said one breast is suspended freely downward through said second breast opening; and
a shield assembly configured to block said chilled air from affecting the temperature of the surface of the patient's other breast when said other breast is suspended freely downward through either of said first and third breast openings.

10. Apparatus as defined in claim 9 further comprising a mirror assembly configured to reflect thermal radiation from said one breast to said sensor.

11. Apparatus as defined in claim 10 wherein said mirror assembly defines an upper reflective surface area having an effectively conical configuration oriented to extend circumferentially around said one breast.

12. Apparatus as defined in claim 11 wherein said mirror assembly further defines a lower reflective surface area oriented to face vertically upward toward said one breast and also toward said upper reflective surface area so as to reflect thermal radiation from said one breast and also from said upper reflective surface area.

13. Apparatus as defined in claim 12 wherein said table is a free standing structure including a table top and a frame upon which said mirror assembly, said air handling system, and said sensor are mounted beneath said table top.

14. Apparatus comprising:
a table having a pair of openings through which a prone patient's breasts can be suspended freely downward;
a thermal radiation sensor;
an air handling system operative to chill ambient air and to direct said chilled air against the suspended breasts; and
a mirror assembly configured to reflect thermal radiation from the suspended breasts to said sensor,
said mirror assembly including a plurality of mirrors oriented to face horizontally inward toward the suspended breasts to reflect thermal radiation from top, bottom and side portions of the suspended breasts to said sensor, and to be inclined vertically downward and horizontally outward from the suspended breasts.

15. Apparatus as defined in claim 14 wherein said mirror assembly further includes a mirror oriented to face vertically upward toward the suspended breasts and also toward said horizontally facing mirrors so as to reflect thermal radiation from the suspended breasts and also from said horizontally facing mirrors.

16. Apparatus comprising:
a table having an opening through which a prone patient's breast can be suspended freely downward;

an air handling system including an air conditioning unit operative to chill ambient air, said air handling system being operative to direct said chilled air against the suspended breast;

a sensor operative to sense temperatures induced on the surface of the suspended breast by said chilled air;

said opening being one of a pair of openings through which a prone patient's breasts can be suspended freely downward; and a breast enclosure structure configured to shield one of the suspended breasts from said chilled air.

17. Apparatus as defined in claim 16 wherein said opening is the second of three breast openings arranged in a row extending across said table and is thus located between first and third breast openings in said row, said breast enclosure structure being one of a pair of breast enclosure structures located beneath said first and third breast openings.

18. Apparatus as defined in claim 16 wherein said air conditioning unit is operative to chill said ambient air to a temperature within a range extending from about 50° F. to about 55° F.

19. Apparatus as defined in claim 16 wherein said sensor is operative to sense thermal radiation emitted by the suspended breast, said apparatus further comprising a mirror assembly configured to reflect said thermal radiation from the suspended breast to said sensor.

* * * * *